United States Patent [19]

Berg

[11] Patent Number: 4,959,128
[45] Date of Patent: Sep. 25, 1990

[54] SEPARATION OF STYRENE FROM ETHYL BENZENE BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 484,413

[22] Filed: Feb. 26, 1990

[51] Int. Cl.$^5$ .......................... B01D 3/40; C07C 7/08
[52] U.S. Cl. ...................................... 203/57; 203/58; 203/60; 585/805; 585/806; 585/808
[58] Field of Search ................ 203/57, 60, 58, 59; 585/860, 806, 805, 808; 208/313

[56] References Cited

U.S. PATENT DOCUMENTS

| | | | |
|---|---|---|---|
| 2,441,827 | 5/1948 | McKinnis | 203/60 |
| 2,477,715 | 8/1949 | Berg et al. | 203/57 |
| 2,494,274 | 1/1950 | Woerner | 203/57 |
| 3,018,228 | 1/1962 | Cornell | 203/58 |
| 3,210,259 | 10/1965 | Cornell et al. | 203/58 |
| 3,684,665 | 8/1972 | Abe et al. | 203/60 |
| 3,763,015 | 6/1973 | Morimoto et al. | 203/60 |
| 4,031,153 | 6/1977 | Haskell | 203/60 |

FOREIGN PATENT DOCUMENTS

| | | | |
|---|---|---|---|
| 135377 | 5/1979 | German Democratic Rep. | 203/58 |
| 49-92030 | 9/1974 | Japan | 203/57 |
| 8200653 | 9/1983 | Netherlands | 585/860 |
| 891604 | 12/1981 | U.S.S.R. | 585/860 |

*Primary Examiner*—Wilbur Bascomb

[57] ABSTRACT

Ethyl benzene cannot be easily removed from styrene by distillation because of the closeness of their boiling points. Ethyl benzene can be readily separated from styrene by means of extractive distillation using certain nitrogenous organic compounds. Typical effective agents are adiponitrile, methyl glutaronitrile and nitrobenzene.

1 Claim, No Drawings

SEPARATION OF STYRENE FROM ETHYL BENZENE BY EXTRACTIVE DISTILLATION

FIELD OF THE INVENTION

This invention relates to a method for separating styrene from ethyl benzene using certain nitrogenous compounds as the agent in extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and this make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Celcius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

Ethyl benzene, B.P.=136.2° C., and styrene, B.P.=145.2° C. have a relative volatility of 1.4 and are thus difficult to separate by rectification. Extractive distillation would be an attractive method of effecting the separation of ethyl benzene from styrene if agents can be found that (1) will enhance the relative volatility of ethyl benzene from styrene and (2) are easy to recover from the styrene, that is, form no azeotrope with styrene and boil sufficiently above styrene to make the separation by rectification possible with only a few theoretical plates.

The advantage of using extractive distillation in this separation can be seen from the data presented in Table 1 below.

TABLE 1

Theoretical and Actual Plates Required vs. Relative Volatility for Ethyl Benzene - Styrene Separation

| Relative Volatility | Theoretical Plates Required At Total Reflux, 99% Purity | Actual Plates Required, 75% Eff. |
|---|---|---|
| 1.4 | 27.5 | 37 |
| 1.6 | 19.5 | 26 |
| 1.8 | 15.7 | 21 |
| 2.0 | 13.3 | 18 |
| 2.2 | 11.7 | 16 |
| 2.4 | 10.5 | 14 |

The relative volatility of ethyl benzene to styrene is 1.4 and thus 27.5 theoretical plates are required for separation to 99% purity by conventional rectification at total reflux. Plates possessing an efficiency of 75% are commonly employed and thus 37 actual plates would be required. One of the agents that I have discovered yields a relative volatility as high as 2.4 which would reduce the plate requirement to only 14.

Extractive distillation typically requires the addition of an equal amount to twice as much extractive agent as the 3-pentanone and formic acid on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with formic acid otherwise it will form a two-phase azeotrope with the formic acid in the recovery column and some other method of separation will have to be employed.

OBJECTIVE OF THE INVENTION

The objects of the invention are to provide a process or method of extractive distillation that will enhance the relative volatility of ethyl benzene to styrene in their separation in a rectification column. It is a further object of this invention to identify certain nitrogenous organic compounds that are stable, can be separated from styrene by rectification with relatively few theoretical plates and can be recycled to the extractive distillation column with little decomposition.

TABLE 2

Effective Extractive Distillation Agents

| Compounds | Ratio: EB:Sty | Relative Volatility |
|---|---|---|
| Adiponitrile | 4:1 | 1.76 |
| " | 7:3 | 1.62 |
| " | 3:2 | 1.47 |
| " | 1:1 | 1.50 |
| " | 4:6 | 1.67 |
| 1,5-Dicyanopentane | 4:1 | 3.10 |
| " | 4:2 | 2.12 |
| " | 4:3 | 1.88 |
| Methyl glutaronitrile | 4:1 | 1.70 |
| " | 4:2 | 2.03 |
| 1,1,3,3-Tetramethyl urea | 4:1 | 1.37 |
| " | 4:2 | 1.41 |
| Nitrobenzene | 4:1 | 1.90 |
| " | 4:2 | 1.47 |
| 2-Nitrotoluene | 4:1 | 1.36 |
| " | 4:2 | 1.92 |
| 3-Nitrotoluene | 4:1 | 1.48 |

TABLE 2-continued

| Effective Extractive Distillation Agents | | |
|---|---|---|
| Compounds | Ratio: EB:Sty | Relative Volatility |
| " | 4:2 | 1.21 |

SUMMARY OF THE INVENTION

The objects of the invention are provided by a process for the separation of ethyl benzene from styrene which entails the use of certain nitrogenous organic compounds as the agent in extractive distillation.

DETAILED DESCRIPTION OF THE INVENTION

I have discovered that certain nitrogenous organic compounds will effectively increase the relative volatility of ethyl benzene to styrene and permit the separation of ethyl benzene from styrene by rectification when employed as the agent in extractive distillation. Table 2 lists compounds that I have found to be effective. The data in Table 2 was obtained in a vapor-liquid equilibrium still. The ratios shown in Table 2 are the parts by weight of ethyl benzene to styrene. The compounds that are effective are adiponitrile, 1,5-dicyanopentane, methyl glutaronitrile, 1,1,3,3-tetramethyl urea, nitrobenzene, 2-nitrotoluene and 3-nitrotoluene.

THE USEFULNESS OF THE INVENTION

The usefulness or utility of this invention can be demonstrated by referring to the data presented in Table 1 and 2. All of the successful extractive distillation agents show that ethyl benzene and styrene can be separated from their mixtures by means of distillation in a rectification column and that the ease of separation as measured by relative volatility is considerable. Without these extractive distillation agents, little improvement will occur in a rectification column. Table 1 shows that these two have a relative volatility of only 1.40. The data also show that the most attractive agents will operate at a boil-up rate low enough to make this a useful and efficient method of recovering high purity ethyl benzene and styrene from any mixture of these two. The stability of the compounds used and the boiling point difference is such that complete recovery and recycle is obtainable by a simple distillation and the amount required for make-up is small.

WORKING EXAMPLES

Example 1

Forty grams of ethyl benzene, ten grams of styrene and forty grams of adiponitrile were charged to a vapor-liquid equilibrium still and refluxed for ¾ hours at 60 mm. Hg. Analysis indicated a vapor composition of 75.9% ethyl benzene, 24.1% styrene, a liquid composition of 64.1% ethyl benzene, 35.9% styrene which is a relative volatility of 1.76.

Example 2

Forty grams of ethyl benzene, 20 grams of styrene and 40 grams of 1,5-dicyanopentane were charged to the vapor-liquid equilibrium still and refluxed for one hour at 60 mm. Hg. Analysis indicated a vapor composition of 53.3% ethyl benzene, 46.7% styrene, a liquid composition of 38% ethyl benzene, 62% styrene which is a relative volatility of 2.12.

Example 3

A glass perforated plate rectification column was calibrated with m-xylene and o-xylene which possesses a relative volatility of 1.11 and found to have 7.3 theoretical plates. A solution comprising 100 grams of ethyl benzene and 100 grams of styrene was placed in the stillpot and heated. When refluxing began, an extractive agent comprising adiponitrile was pumped into the column at a rate of 15 ml/min at 60 mm. Hg absolute pressure. The boil-up rate was 20 ml/min. and the temperature of the extractive agent as it entered the column was 65° C. After establishing the feed rate of the extractive agent, the heat input to the ethyl benzene and styrene in the stillpot was adjusted to give a total reflux rate of 10–20 ml/min. After one hour of operation, the overhead and bottoms samples of approximately two ml. were collected and analysed by gas chromatography. The overhead analysis was 97.1% ethyl benzene, 2.9% styrene. The bottoms analysis was 42% ethyl benzene styrene. Using these compositions in the Fenske equation with the number of plates in the column being 7.3, gave an average relative volability of 1.695 for each theoretical plate.

I claim:

1. A method for recovering ethyl benzene from mixtures of ethyl benzene and styrene which comprises distilling a mixture of ethyl benzene and styrene in a rectification column in the presence of about one part of an extractive agent per part of ethyl benzene—styrene mixture, recovering ethyl benzene as overhead and styrene and the extractive agent from the stillpot, wherein said extractive agent is one member selected from the group consisting of adiponitrile, 1,5-dicyanopentane, methyl glutaronitrile, nitrobenzene, 2-nitrotoluene and 3-nitrotoluene.

* * * * *